United States Patent
Zhao et al.

(10) Patent No.: US 11,414,375 B2
(45) Date of Patent: *Aug. 16, 2022

(54) MILD AND EFFICIENT PREPARATION METHOD FOR α-ACYLOXYENAMIDE COMPOUNDS AND USE THEREOF IN SYNTHESIS OF AMIDE AND POLYPEPTIDE

(71) Applicant: Jiangxi Normal University, Nanchang (CN)

(72) Inventors: Junfeng Zhao, Nanchang (CN); Long Hu, Nanchang (CN); Silin Xu, Nanchang (CN); Zhenguang Zhao, Nanchang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,435

(22) Filed: Jun. 5, 2020

(65) Prior Publication Data

US 2020/0299226 A1    Sep. 24, 2020

Related U.S. Application Data

(62) Division of application No. 16/311,747, filed as application No. PCT/CN2017/071910 on Jan. 20, 2017, now Pat. No. 10,836,707.

(30) Foreign Application Priority Data

Jul. 29, 2016  (CN) .......................... 201610606375.1

(51) Int. Cl.

| | |
|---|---|
| C07C 219/20 | (2006.01) |
| C07C 303/40 | (2006.01) |
| C07D 231/56 | (2006.01) |
| C07D 333/68 | (2006.01) |
| C07C 311/17 | (2006.01) |
| C07C 231/02 | (2006.01) |
| C07C 233/05 | (2006.01) |
| C07D 263/22 | (2006.01) |
| C07D 209/20 | (2006.01) |
| C07D 307/68 | (2006.01) |
| C07C 269/06 | (2006.01) |
| C07C 239/22 | (2006.01) |
| C07D 209/14 | (2006.01) |
| C07D 295/13 | (2006.01) |
| C07K 5/078 | (2006.01) |
| C07D 295/192 | (2006.01) |
| C07D 493/10 | (2006.01) |
| C07K 5/062 | (2006.01) |
| C07K 5/072 | (2006.01) |
| C07D 495/04 | (2006.01) |
| C07C 213/08 | (2006.01) |

(52) U.S. Cl.
CPC .......... *C07C 219/20* (2013.01); *C07C 213/08* (2013.01); *C07C 231/02* (2013.01); *C07C 233/05* (2013.01); *C07C 239/22* (2013.01); *C07C 269/06* (2013.01); *C07C 303/40* (2013.01); *C07C 311/17* (2013.01); *C07D 209/14* (2013.01); *C07D 209/20* (2013.01); *C07D 231/56* (2013.01); *C07D 263/22* (2013.01); *C07D 295/13* (2013.01); *C07D 295/192* (2013.01); *C07D 307/68* (2013.01); *C07D 333/68* (2013.01); *C07D 493/10* (2013.01); *C07D 495/04* (2013.01); *C07K 5/06069* (2013.01); *C07K 5/06113* (2013.01); *C07K 5/06156* (2013.01); *C07B 2200/07* (2013.01); *C07C 2603/18* (2017.05); *C07C 2603/74* (2017.05)

(58) Field of Classification Search
None
See application file for complete search history.

(56) References Cited

PUBLICATIONS

Xu, Shijie. Metal-free hydroacyloxylation and hydration reactions of ynamides: synthesis of alpha-acyloxyenamides and N-acylsulfonamides. Green Chemistry 16(9), 2014.*

* cited by examiner

*Primary Examiner* — Samantha L Shterengarts
(74) *Attorney, Agent, or Firm* — Novoclaims Patent Services LLC; Mei Lin Wong

(57) ABSTRACT

Disclosed are a mild and efficient preparation method for an α-acyloxyenamide compound and a use thereof in the synthesis of an amide and a polypeptide. The α-acyloxyenamide compound is obtained by an addition reaction of a ynamide and a carboxylic acid in dichloromethane under conditions where the temperature is 0° C. to 50° C.; the produced α-acyloxyenamide compound can react with an amine compound to produce an amide or a polypeptide; the two reactions can be carried out step by step, and can also be carried out in one pot. According to the invention, the reaction conditions are mild and no metal catalyst is required; when the carboxylic acid, which has chirality on an alpha site of carboxyl, forms an amide bond or a peptide bond, no racemization occurs; and the operation is simple and the application range is wide.

7 Claims, No Drawings

MILD AND EFFICIENT PREPARATION METHOD FOR α-ACYLOXYENAMIDE COMPOUNDS AND USE THEREOF IN SYNTHESIS OF AMIDE AND POLYPEPTIDE

CROSS REFERENCES OF RELATED APPLICATIONS

This is a divisional application of a non-provisional application Ser. No. 16/311,747, filing date of Dec. 20, 2018, which is a national phase application under 371 of PCT/CN2017/071910, filing date Jan. 20, 2017 claiming the priority of Chinese application number 201610606375.1, filing date Jul. 29, 2016. The content of these specification, including any intervening amendments thereto, are incorporated herein by reference.

BACKGROUND OF THE INVENTION

Technical Field

The invention relates to the preparation of α-acyloxyenamide compounds and a use thereof in the synthesis of an amide and a polypeptide, in particular to a method for efficiently preparing α-acyloxyenamide compounds at room temperature and without metal catalysis and a method for synthesizing an amide or a polypeptide by reacting an α-acyloxyenamide compound with a primary or secondary amine compound (stepwise or one-pot method).

Description of Related Art

Amide bonds are the most common chemical bond in nature and a very important type of functional group in organic chemistry. Amide bonds are widely present in various functional materials, pharmaceuticals, agrochemicals and other fine chemical raw materials. It is reported that one-quarter of the marketed pharmaceuticals contain amide bonds, and 16% of organic reactions involve the formation of amide bonds. An amide bond is also the basic structural unit of protein and plays an important role in regulating various life activities and physiological processes. For example, various enzyme proteins in the living body are of great significance to the life activities of the organism. An amide bond can be formed by dehydration condensation of a carboxylic acid with a primary or secondary amine, but this seemingly simple reaction is not so easy to execute. Conventional methods for synthesizing amides are accomplished by activating a carboxylic acid, such as the formation of an acid chloride, an anhydride or other active esters, followed by a nucleophilic substitution reaction with an amine to form an amide. Among many coupling reagents and activating reagents, most of them have the disadvantages of low coupling efficiency, high price, ease of racemization, and the like, and the formation of amide bonds faces many problems. Therefore, the green, atom-economic synthesis of amides has been selected as the biggest challenge for organic synthesis in the 21st century (D. J. C. Constable, Green Chem., 2007, 9, 411). In recent years, with the slow development of new organic small molecule drugs, peptides and protein drugs and diagnostic reagents have received more and more attention due to their lower toxicity and fewer side effects. Polypeptides have also become an important source for the development of new drugs. However, the prices of polypeptides are still very high, which affects their wide application to some extent. The reason for the high prices of the polypeptides we analyze is mainly attributed to coupling reagents, reaction solvents, and purification costs used in the synthesis of polypeptides, and the raw material amino acid is very cheap. Therefore, innovatives in coupling reagents, protecting groups, reaction solvents and purification methods are urgently demanded. This requires organic chemists to develop efficient, mild, low-cost and atom-economic methods of forming an amide bond and a peptide bond that is unlikely to have racemization and meet the requirements for the development of modern chemical industry as soon as possible. Although many amide bond formation strategies have been developed, the dehydration condensation between carboxylic acids and amines is still the most realiable method considering the source and cost of the raw materials. Therefore, the development of efficient and atom-economic amide bond coupling reagents is still an effective approach and major challenge to the problems faced by amide bond synthesis at present.

Ynamines have been used as amide bond coupling reagents, but since the ynamines are difficult to synthesize and sensitive to water, air, etc., and their intermediates formed with carboxylic acids are also unstable and easily hydrolyzed, and serious racemization observed in the formation of peptide bonds resulted the ynamine coupling reagents be eventually abandoned by peptide community (Viehe, H. G., Angew. Chem. Int. Ed. 1964, 3, 582; Arens, J. F., Recl. Tray. Chim. Pays-Bas 1965, 84, 1344; Gais, H.-J., Angew. Chem. Int. Ed. 1978, 17, 597; Neuenschwander, M., Helv. Chim. Acta 1978, 61, 2428; 2437). Our research group found that the addition product α-acyloxyenamide of a carboxylic acid and an ynamide is also a type of active ester, which can form an amide through a highly efficient nucleophilic reaction with an amine. Compared with a ynamine, a ynamide contains an electron-withdrawing group on the nitrogen atom, which greatly enhances its thermal stability, reduces its sensitivity to water and oxygen, and improves operability. More importantly, the introduction of the electron-withdrawing group greatly reduces the basicity of the ynamine, which means that the problem of chiral acid racemization caused by basicity will be suppressed. Therefore, we believe that ynamides will become efficient and practical amide coupling reagents for amide and peptide synthesis.

If the addition reaction of a carboxylic acid and a ynamide can be carried out under mild and simple conditions, we will be able to successfully develop a new method for forming an amide bond by using a ynamide as a coupling reagent. However, there are only two reports related to the addition reaction of a carboxylic acid and a ynamide, and the reaction conditions are harsh. In 2012, the Lam and co-workers reported that an α-acyloxyenamide could be constructed from the addition reaction of a carboxylic acid and a ynamide in the presence of palladium-catalyst α-acyloxyenamide for the first time (Chem. Commun. 2012, 48, 1505-1507). In 2015, the Bi and co-workers found that the addition of a carboxylic acid and a ynamide can be carried out without metal catalysis (Green Chemistry 2015, 17, 184-187), but the reaction should be carried out at a high temperature of 100° C., and some compounds unstable under such high temperature conditions cannot be prepared by this method. In order to achieve a ynamide-mediated amide bond formation process under mild conditions, we first need to develop a method for synthesizing α-acyloxyenamide compounds by the addition reaction of a carboxylic acid and a ynamide under mild reaction conditions.

BRIEF SUMMARY OF THE INVENTION

The object of the invention is to solve the problem of the harsh addition conditions of a carboxylic acid and a ynamide in the prior art and to fill in the application blank of the α-acyloxyenamide compounds in forming an amide bond or a peptide bond, and provide a mild and efficient preparation method for α-acyloxyenamide compounds, and use of the α-acyloxyenamide compounds in the synthesis of an amide and a polypeptide.

We first conducted a systematic and extensive study on the addition reaction of a carboxylic acid and a ynamide, and then found that the reaction is very sensitive to solvents. In a solvent, such as N,N-dimethylformamide, N,N-dimethylacetamide, 1,4-dioxane and tetrahydrofuran, at room temperature and without metal catalysis, substantially no reaction occurs; in acetone, acetonitrile and methanol, a reaction can occur, but slowly. The best reaction efficiency is achieved in a halogenated hydrocarbon solvent, such as dichloromethane, 1,2-dichloromethane and chloroform. The reaction can be finished in 1-2 hours at room temperature and the product yield can reach almost 100%. Our further studies disclosed that α-acyloxyenamide compounds are active esters which can react with primary or secondary amines at room temperature to produce amides and polypeptides. The addition reaction of a carboxylic acid a ynamide and the subsequent aminolysis reaction of an α-acyloxyenamide compound with an amine can be carried out stepwise or by a "one-pot" method. We have also found that the aminolysis reaction of an α-acyloxyenamide with an amine to form an amide can be carried out by using water as a solvent, and the reaction rate is 10 times faster than in an organic solvent such as dichloromethane, and chiral a acid does not have racemization. Therefore, we have summarized that the invention is achieved in the following manner.

In the first part of the invention, a mild and efficient preparation method for an α-acyloxyenamide compound is provided, comprising the following steps:

(1) adding 0.2-2 mmol of a ynamide and an appropriate amount of dichloromethane solvent to a clean reaction tube, and then adding 0.2-2 mmol of carboxylic acid, and stirring at a temperature of 0-50° C.; and (2) detecting the previous step of the reaction by using a TLC ananlysis; after the previous step of the reaction is completed, the reaction mixture was concentrated under vacuum. A pure α-acyloxyenamide compound could be obtained via column chromatography.

The chemical reaction formula of step (1) is:

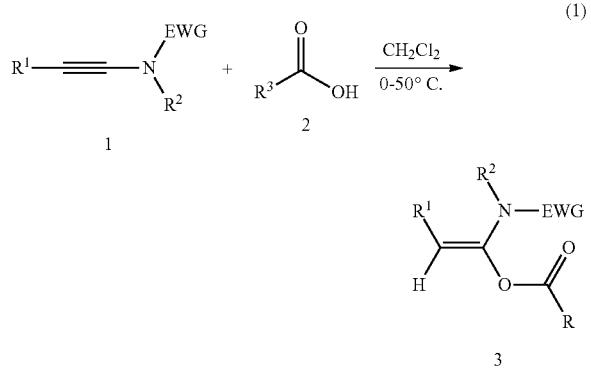

In the formula, 1 represents a ynamide, 2 represents a carboxylic acid, 3 represents an α-acyloxyenamide compound; $R^1$ may be a hydrogen atom, an alkyl group, an aryl group, an alkoxy group, an alkylthio group or the like, the EWG (electron-withdrawing group) may be an alkylsulfonyl group, an arylsulfonyl group, an aryl group, a carbonyl group, a nitro group, a nitrile group, a phosphono group or the like, and $R^2$ may be an alkyl group or an aryl group.

In the preparation method, the carboxylic acid may be a carboxylic acid such as an aliphaticacid, an aromatic acid (such as fluorescein and rhodamine), a heterocyclic acid, an acetylenic acid, an olefinic acid, an α-amino acid, or a β-amino acid.

In the preparation method, the molar ratio of the ynamide to the carboxylic acid is 0.1-10.

In the preparation method, dichloromethane is used as a solvent and can be replaced with a solvent such as chloroform or 1,2-dichloroethane.

In the preparation method, the optimum temperature for the reaction is 25° C.

In the second part of the invention, provided is use of an α-acyloxyenamide compound in the synthesis of an amide and a polypeptide, comprising the following steps:

(1) adding 0.2-2 mmol of an α-acyloxyenamide compound and an appropriate amount of dichloromethane solvent to a clean reaction tube, and then adding 0.2-2 mmol of an amine compound, and stirring at a temperature of 0-50° C.

(2) detecting the previous step of the reaction by using a TLC analysis; after the previous step of the reaction is completed, and separating and purifying by column chromatography to directly obtain an amide compound.

wherein the chemical reaction formula of Step (2) is:

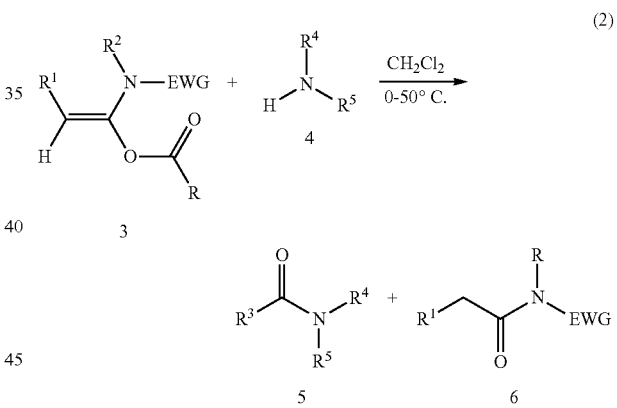

In the formula, 3 represents an α-acyloxyenamide compound, 4 represents an amine compound, 5 represents an amide compound, 6 represents an amide by-product; $R^1$ may be a hydrogen atom, an alkyl group, an aryl group, an alkoxy group, an aryloxy group, an alkylthio group, an arylthio group, or the like; the EWG (electron-withdrawing group) may be an alkylsulfonyl group, an arylsulfonyl group, an aryl group, a carbonyl group, a nitro group, a nitrile group, a phosphono group, a sulfonimide, or the like; $R^2$ may be alkyl or aryl, $R^3$ may be an alkyl group, an aryl group, an alkenyl group, an alkynyl group, or the like; $R^4$ may be hydrogen, an aliphatic substituent or an aromatic substituent; $R^5$ may be a hydrogen atom, an aliphatic substituent, or an aromatic substituent.

In the use method, the amine compound may be a primary or secondary amine, including an aliphatic amine and an aromatic amine.

In the use method, the ratio of the α-acyloxyenamide compound to the amine compound is 0.1-10.

In the use method, dichloromethane is used as a solvent and can be replaced with water, or replaced with an organic solvent such as chloroform or 1,2-dichloroethane, or replaced with a mixture of water and dimethylsulfoxide, or a mixture of water and N,N-dimethylformamide.

In the use method, the optimum temperature for the reaction is 35° C.

In the third part of the invention, a method (one-pot) for synthesizing an amide and a polypeptide by directly using a carboxylic acid and an amine compound as raw materials and under the mediation of an ynamide is provided, comprising the following steps:

(1) adding 0.2-2 mmol of a carboxylic acid and an appropriate amount of dichloromethane solvent to a clean reaction tube, and then adding 0.2-2 mmol of an ynamide, and stirring at a temperature of 0-50° C.;

(2) detecting the previous step of the reaction by using a TLC analysis; after the previous step of the reaction is completed, directly adding 0.2-2 mmol of an amine compound, or removing the solvent used in the previous step and adding water as a solvent and then adding 0.2-2 mmol of an amine compound, and then stirring at a temperature of 0-50° C.; and (3) detecting the previous step of the reaction by using a TLC analysis; after the previous step of the reaction is completed, and separating and purifying by column chromatography to directly obtain an amide compound.

wherein the chemical reaction formula of step (1) and step (2) is:

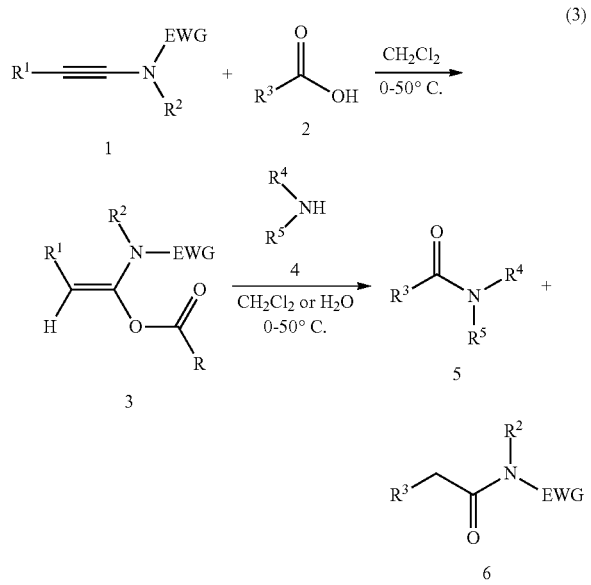

In the formula, 1 represents a ynamide, 2 represents a carboxylic acid, 3 represents an α-acyloxyenamide compound, 4 represents an amine compound, 5 represents an amide compound, 6 represents an amide by-product; $R^1$ may be a hydrogen atom, an alkyl group, an aryl group, an alkoxy group, an aryloxy group, an alkylthio group, an arylthio group, or the like; the EWG (electron-withdrawing group) may be an alkylsulfonyl group, an arylsulfonyl group, a carbonyl group, an alkynyl group, a nitro group, a nitrile group, a phosphono group, a sulfonimide, or the like; $R^2$ may be alkyl or aryl, $R^3$ may be an alkyl group, an aryl group, an alkenyl group, an alkynyl group, or the like; $R^4$ may be a hydrogen atom, an aliphatic substituent or an aromatic substituent; $R^5$ may be a hydrogen atom, an aliphatic substituent, or an aromatic substituent.

In the method, the carboxylic acid may be a carboxylic acid such as a aliphatic acid, an aromatic acid (such as fluorescein and rhodamine), a heterocyclic acid, an acetylenic acid, an olefine acid, an α-amino acid, or a β-amino acid.

In the method, the optimum ratio of the carboxylic acid to the ynamide to the amine compound is 1:1.2:1.2.

In the method, Step (1) uses dichloromethane as a solvent which may be replaced with an organic solvent such as chloroform, 1,2-dichloroethane or methanol; the solvent in Step (2) may be an organic solvent such as dichloromethane, chloroform or 1,2-dichloroethane, and may also be water, or a mixture of water and dimethylsulfoxide, or a mixture of water and N,N-dimethylformamide.

In the method, the optimum temperature for the reaction of Step (1) is 25° C., and the optimum temperature for the reaction of Step (2) is 35° C.

The beneficial effects of the invention are as follows: (1) an α-acyloxyenamide compound is synthesized by using a simple ynamide and carboxylic acid at room temperature and without metal catalysis, so that the synthesis of the α-acyloxyenamide compound is milder and more direct and concise, and its potential application can be better reached; (2) an amide bond is synthesized by using an α-acyloxyenamide compound and a primary or secondary amine compound, wherein the α-acyloxyenamide compound especially refers to an α-acyloxyenamide formed by a natural α-amino acid and other chiral acids with a ynamide; this method not only can effectively control the problem of chiral acid racemization during synthesis, but also make the synthesis of an amide bond and a peptide bond more concise and efficient; (3) an amide bond is formed from a simple carboxylic acid and amine compound in the presence of a ynamide as a coupling reagent by a "one-pot method", which is more convenient to operate and has broad industrial application; and (4) the reaction of an α-acyloxyenamide compound and an amine compound can be carried out in water, thereby avoiding the use of an organic solvent, greatly improving production safety and reducing production costs, and also providing a new method for modifying and labeling biological macromolecules such as proteins and nucleic acids in a site-directed mode.

DETAILED DESCRIPTION OF THE INVENTION

The advantages of the invention are described in detail below with reference to Embodiments 1 to 39, which are intended to help the reader to better understand the essence of the invention, but do not limit the implementation and the scope of the invention.

The first part refers to specific embodiments (Embodiments 1 to 23) of a mild and efficient preparation method for an α-acyloxyenamide compound, and the Applicant believes that Embodiment 10 is optimal.

Embodiment 1

N-methyl-N-ethynyl p-toluenesulfonamide (0.20 mmol) and formic acid (2 mmol) are added to a clean 25 mL reaction tube, and an appropriate amount of dichloromethane is added as a solvent. The reaction is carried out at 10° C. for 10 minutes. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

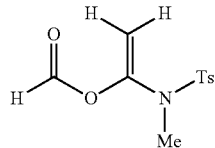

$^1$H NMR (400 MHz, CDCl$_3$) δ 8.06 (s, 1H), 7.71 (d, J=8.3 Hz, 2H), 7.33 (t, J=7.5 Hz, 3H), 4.83 (d, J=2.9 Hz, 1H), 4.73 (d, J=2.8 Hz, 1H), 3.01 (s, 3H), 2.43 (s, 3H).

$^{13}$C NMR (100 MHz, CDCl$_3$) δ 158.2, 146.9, 144.4, 134.1, 129.6, 127.8, 99.7, 36.8, 21.5 ppm.

HRMS m/z (ESI) calcd for C$_{11}$H$_{14}$NO$_4$S (M+H)$^+$: 256.0644, found: 256.0647.

Embodiment 2

N-methyl-N-ethynyl p-toluenesulfonamide (0.20 mmol) and adamantanecarboxylic acid (0.3 mmol) are added to a clean 25 mL reaction tube, and an appropriate amount of dichloromethane is added as a solvent. The reaction is carried out at 0° C. for 4 hours. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

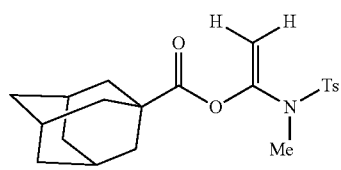 [SMILES: C=C(OC(=O)C12CC3CC(CC(C3)C1)C2)N(C)S(=O)(=O)c1ccc(C)cc1]

$^1$H NMR (400 MHz, CDCl$_3$) δ 7.73 (d, J=8.3 Hz, 2H), 7.32 (d, J=8.1 Hz, 2H), 4.83 (d, J=2.2 Hz, 1H), 4.79 (d, J=2.2 Hz, 1H), 2.95 (s, 3H), 2.42 (s, 3H), 1.97 (s, 3H), 1.75 (d, J=2.5 Hz, 6H), 1.70 (d, J=12.4 Hz, 3H), 1.63 (d, J=12.1 Hz, 3H).

$^{13}$C NMR (100 MHz, CDCl$_3$) δ 174.8, 146.5, 143.9, 134.1, 129.5, 128.1, 102.0, 41.0, 38.3, 36.6, 36.2, 27.7, 21.5 ppm.

HRMS m/z (ESI) calcd for C$_{21}$H$_{28}$NO$_4$S (M+H)$^+$: 390.1739, found: 390.1735.

Embodiment 3

N-methyl-N-ethynyl p-toluenesulfonamide (0.30 mmol) and parachlorobenzoic-acid (0.2 mmol) are added to a clean 25 mL reaction tube, and an appropriate amount of dichloromethane is added as a solvent. The reaction is carried out at room temperature for κ hours. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

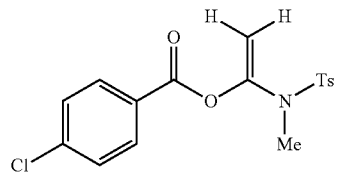 [SMILES: C=C(OC(=O)c1ccc(Cl)cc1)N(C)S(=O)(=O)c1ccc(C)cc1]

$^1$H NMR (400 MHz, CDCl$_3$) δ 7.83 (d, J=8.6 Hz, 2H), 7.73 (d, J=8.2 Hz, 2H), 7.39 (d, J=8.5 Hz, 2H), 7.27 (d, J=8.1 Hz, 2H), 5.02 (d, J=2.5 Hz, 1H), 4.83 (d, J=2.6 Hz, 1H), 3.10 (s, 3H), 2.40 (s, 3H).

$^{13}$C NMR (100 MHz, CDCl$_3$) δ 163.1, 146.9, 144.0, 140.3, 134.1, 131.5, 129.5, 128.8, 127.9, 127.1, 101.4, 37.3, 21.5 ppm.

HRMS m/z (ESI) calcd for C$_{17}$H$_{17}$ClNO$_4$S (M+H)$^+$: 366.0567, found: 366.0563.

Embodiment 4

N-methyl-N-ethynyl p-toluenesulfonamide (0.20 mmol) and furoic acid (0.2 mmol) are added to a clean 25 mL reaction tube, and an appropriate amount of dichloromethane is added as a solvent. The reaction is carried out at room temperature for 30 minutes. TLC analysis is then performed. After the completion of the reaction, the solvent was concentrated off and the column chromatography are carried out to obtain a pure product, white solid, with a yield of 98%. The following are the structural formula of the product and the NMR data and mass spectrometry data of the product:

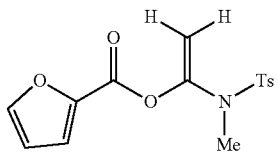 [SMILES: C=C(OC(=O)c1ccco1)N(C)S(=O)(=O)c1ccc(C)cc1]

$^1$HNMR (400 MHz, CDCl$_3$) δ 7.66 (d, J=8.0 Hz, 2H), 7.54 (s, 1H), 7.20 (d, J=8.2 Hz, 2H), 7.02 (d, J=3.2 Hz, 1H), 6.44 (s, 1H), 4.94 (d, J=2.1 Hz, 1H), 4.75 (d, J=2.1 Hz, 1H), 2.99 (s, 3H), 2.32 (s, 3H).

$^{13}$C NMR (100 MHz, CDCl$_3$) δ 155.6, 147.4, 146.3, 144.0, 143.1, 134.0, 129.4, 127.9, 119.8, 112.1, 101.7, 37.2, 21.5 ppm.

HRMS m/z (ESI) calcd for C$_{15}$H$_{16}$NO$_5$S (M+H)$^+$: 322.0749, found: 322.0754.

Embodiment 5

N-methyl-N-ethynyl p-toluenesulfonamide (2.0 mmol) and 1-methylindazole-3-carboxylic acid (0.2 mmol) are added to a clean 25 mL reaction tube, and an appropriate amount of chloroform is added as a solvent. The reaction is carried out at room temperature for 5 hours. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

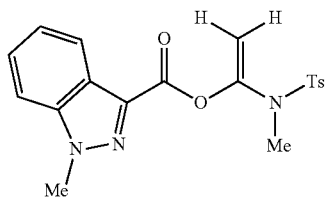 [SMILES: C=C(OC(=O)c1nn(C)c2ccccc12)N(C)S(=O)(=O)c1ccc(C)cc1]

¹H NMR (400 MHz, CDCl₃) δ 7.96 (d, J=8.2 Hz, 1H), 7.78 (d, J=8.2 Hz, 2H), 7.47 (d, J=2.7 Hz, 2H), 7.34-7.27 (m, 1H), 7.21 (d, J=8.1 Hz, 2H), 5.08 (d, J=2.4 Hz, 1H), 4.90 (d, J=2.4 Hz, 1H), 4.18 (s, 3H), 3.15 (s, 3H), 2.33 (s, 3H).

¹³C NMR (100 MHz, CDCl₃) δ 159.8, 146.5, 143.8, 141.0, 134.4, 133.1, 129.4, 128.0, 127.0, 123.7, 123.5, 122.0, 109.6, 101.6, 37.2, 36.5, 21.5 ppm.

HRMS m/z (ESI) calcd for $C_{19}H_{20}N_3O_4S$ (M+H)⁺: 386.1175, found: 386.1173.

Embodiment 6

N-methyl-N-ethynyl p-toluenesulfonamide (1.0 mmol) and 1-benzothiophene-3-carboxylic acid (0.2 mmol) are added to a clean 25 mL reaction tube, and an appropriate amount of dichloromethane is added as a solvent. The reaction is carried out at 40° C. for 1 hour. TLC analysis is then performed. After the completion of the reaction, the solvent was concentrated off and the column chromatography are carried out to obtain a pure product, white solid, with a yield of 100%. The following are the structural formula of the product and the NMR data and mass spectrometry data of the product:

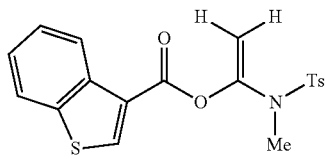 [SMILES: C=C(OC(=O)c1csc2ccccc12)N(C)S(=O)(=O)c1ccc(C)cc1]

¹H NMR (400 MHz, CDCl₃) δ 7.92 (s, 1H), 7.86 (d, J=8.1 Hz, 2H), 7.76 (d, J=8.2 Hz, 2H), 7.50-7.41 (m, 2H), 7.29-7.24 (m, 2H), 5.09 (d, J=2.5 Hz, 1H), 4.92 (d, J=2.5 Hz, 1H), 3.12 (s, 3H), 2.33 (s, 3H).

¹³C NMR (100 MHz, CDCl₃) δ 160.0, 146.5, 144.0, 142.7, 138.4, 134.3, 132.1, 131.6, 129.6, 127.9, 127.5, 125.7, 125.1, 122.7, 101.9, 37.1, 21.4 ppm.

HRMS m/z (ESI) calcd for $C_{19}H_{18}NO_4S_2$ (M+H)⁺: 388.0677, found: 388.0676.

Embodiment 7

N-methyl-N-ethynyl p-toluenesulfonamide (0.80 mmol) and cinnamic acid (0.2 mmol) are added to a clean 25 mL reaction tube, and an appropriate amount of 1,2-dichloroethane is added as a solvent. The reaction is carried out at 50° C. for 1 hour. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

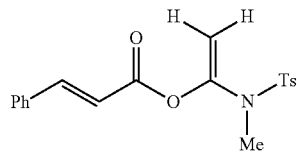 [SMILES: C=C(OC(=O)/C=C/c1ccccc1)N(C)S(=O)(=O)c1ccc(C)cc1]

¹H NMR (400 MHz, CDCl₃) δ 7.75 (d, J=8.3 Hz, 2H), 7.59 (d, J=16.0 Hz, 1H), 7.51-7.45 (m, 2H), 7.44-7.38 (m, 3H), 7.30 (d, J=8.0 Hz, 2H), 6.31 (d, J=16.0 Hz, 1H), 4.95 (d, J=2.4 Hz, 1H), 4.78 (d, J=2.5 Hz, 1H), 3.08 (s, 3H), 2.36 (s, 3H).

¹³C NMR (100 MHz, CDCl₃) δ 164.1, 147.0, 146.9, 144.0, 134.5, 133.9, 130.8, 129.5, 129.0, 128.3, 128.0, 116.3, 101.1, 37.2, 21.5 ppm.

HRMS m/z (ESI) calcd for $C_{19}H_{20}NO_4S$ (M+H)⁺: 358.1113, found: 358.1110.

Embodiment 8

N-methyl-N-ethynyl p-toluenesulfonamide (0.80 mmol) and phenylpropiolic acid (0.2 mmol) are added to a clean 25 mL reaction tube, and an appropriate amount of dichloromethane is added as a solvent. The reaction is carried out at 0° C. for 10 minutes. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

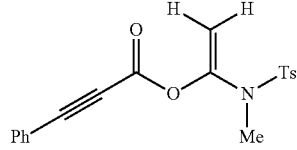 [SMILES: C=C(OC(=O)C#Cc1ccccc1)N(C)S(=O)(=O)c1ccc(C)cc1]

¹HNMR (400 MHz, CDCl₃) δ 7.76 (d, J=8.2 Hz, 2H), 7.62-7.55 (m, 2H), 7.49 (t, J=7.5 Hz, 1H), 7.40 (t, J=7.5 Hz, 2H), 7.31 (d, J=8.1 Hz, 2H), 4.99 (d, J=2.7 Hz, 1H), 4.81 (d, J=2.7 Hz, 1H), 3.07 (s, 3H), 2.39 (s, 3H).

¹³C NMR (100 MHz, CDCl₃) δ 151.0, 146.4, 144.1, 134.1, 133.1, 131.1, 129.6, 128.6, 128.0, 119.0, 101.8, 89.4, 79.5, 37.2, 21.5 ppm.

HRMS m/z (ESI) calcd for $C_{19}H_{18}NO_4S$ (M+H)⁺: 356.0957, found: 356.0955.

Embodiment 9

N-methyl-N-ethynyl p-toluenesulfonamide (0.20 mmol) and N-benzyloxycarbonyl-L-serine (0.2 mmol) are added to a clean 25 mL reaction tube, and an appropriate amount of dichloromethane is added as a solvent. The reaction is carried out at 30° C. for 30 minutes. TLC analysis is then performed. After the completion of the reaction, the solvent was concentrated off and the column chromatography are carried out to obtain a pure product, solid, with a yield of 99%. The following are the structural formula of the product and the NMR data and mass spectrometry data of the product:

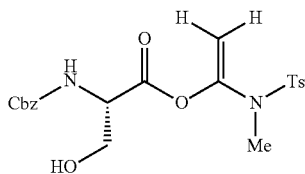 [SMILES: C=C(OC(=O)[C@H](CO)NC(=O)OCc1ccccc1)N(C)S(=O)(=O)c1ccc(C)cc1]

¹HNMR (400 MHz, CDCl₃) δ 7.71 (d, J=8.2 Hz, 2H), 7.36-7.32 (m, 7H), 5.84 (d, J=8.4 Hz, 1H), 5.19-5.09 (m, 2H), 4.87 (d, J=2.5 Hz, 1H), 4.46 (dd, J=15.5, 5.5 Hz, 2H), 4.28-4.16 (m, 1H), 3.85 (dd, J=11.8, 3.2 Hz, 1H), 2.98 (s, 3H), 2.43 (s, 3H).

¹³C NMR (100 MHz, CDCl₃) δ 168.2, 156.2, 147.0, 144.6, 136.1, 132.0, 129.6, 128.5, 128.1, 128.0, 127.3, 100.5, 67.1, 62.6, 56.3, 38.0, 21.6 ppm.

HRMS m/z (ESI) calcd for $C_{21}H_{25}N_2O_7S$ (M+H)⁺: 449.1382, found: 449.1385.

Embodiment 10

N-methyl-N-ethynyl p-toluenesulfonamide (0.20 mmol) and Fmoc-L-threonine (0.2 mmol) are added to a clean 25 mL reaction tube, and an appropriate amount of dichloromethane is added as a solvent. The reaction is carried out at room temperature for 40 minutes. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

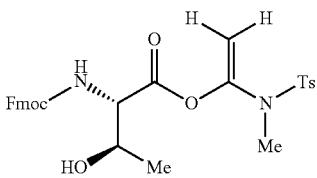

1H NMR (400 MHz, CDCl₃) δ7.77-7.7 (m, 4H), 7.64 (t, J=7.5 Hz, 2H), 7.43-7.37 (m, 2H), 7.32 (d, J=7.9 Hz, 4H), 5.84 (d, J=9.4 Hz, 1H), 4.89 (d, J=2.8 Hz, 1H), 4.61-4.51 (m, 1H), 4.47-4.39 (m, 4H), 4.26 (t, J=7.2 Hz, 1H), 2.99 (s, 3H), 2.42 (s, 3H), 1.30 (d, J=6.4 Hz, 3H).

13C NMR (100 MHz, CDCl₃) δ 168.5, 156.7, 147.0, 144.5, 141.2, 141.2, 132.0, 129.5, 128.1, 127.6, 127.0, 125.1, 119.9, 100.7, 67.3, 67.0, 59.6, 47.0, 38.0, 21.5, 19.5 ppm.

HRMS m/z (ESI) calcd for $C_{29}H_{31}N_2O_7S$ (M+H)+: 551.1852, found: 551.1856.

Embodiment 11

N-methyl-N-ethynyl p-toluenesulfonamide (0.20 mmol) and N-benzyloxycarbonyl-L-tryptophan (0.24 mmol) are added to a clean 25 mL reaction tube, and an appropriate amount of dichloromethane is added as a solvent. The reaction is carried out at room temperature for 30 minutes. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

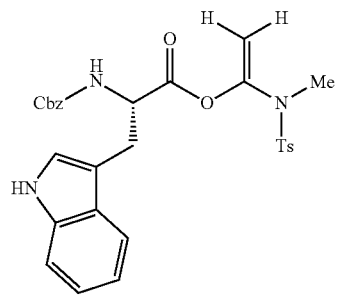 [SMILES: C=C(OC(=O)[C@H](Cc1c[nH]c2ccccc12)NC(=O)OCc1ccccc1)N(C)S(=O)(=O)c1ccc(C)cc1]

¹H NMR (400 MHz, CDCl₃) δ 8.28 (s, 1H), 7.67 (d, J=8.2 Hz, 2H), 7.54 (d, J=7.8 Hz, 1H), 7.43-7.26 (m, 6H), 7.23-7.18 (m, 3H), 7.11 (t, J=7.5 Hz, 1H), 7.03 (d, J=11.2 Hz, 1H), 5.29 (t, J=25.3 Hz, 1H), 5.08 (q, J=12.2 Hz, 2H), 4.85 (d, J=1.9 Hz, 1H), 4.76-4.55 (m, 2H), 3.47-3.12 (m, 2H), 2.90 (d, J=15.5 Hz, 3H), 2.36 (s, 3H).

¹³C NMR (100 MHz, CDCl₃) δ 169.5, 155.7, 146.6, 144.3, 136.1, 133.4, 129.5, 128.5, 128.1, 128.0, 127.9, 127.5, 123.3, 122.2, 119.7, 118.5, 111.3, 109.2, 101.9, 67.0, 54.7, 37.0, 27.3, 21.5 ppm.

HRMS m/z (ESI) calcd for $C_{29}H_{30}N_3O_6S$ (M+H)⁺: 548.1855, found: 548.1856.

Embodiment 12

N-methyl-N-ethynyl p-toluenesulfonamide (0.20 mmol) and N-tert-butoxycarbonyl-L-phenylalanine (0.2 mmol) are added to a clean 25 mL reaction tube, and an appropriate amount of dichloromethane is added as a solvent. The reaction is carried out at room temperature for 30 minutes. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

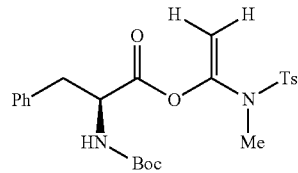 [SMILES: C=C(OC(=O)[C@H](Cc1ccccc1)NC(=O)OC(C)(C)C)N(C)S(=O)(=O)c1ccc(C)cc1]

¹H NMR (400 MHz, CDCl₃) δ 7.72 (d, J=8.2 Hz, 2H), 7.33-7.22 (m, 5H), 7.15 (d, J=7.0 Hz, 2H), 4.92-4.87 (m, 2H), 4.70 (s, 1H), 4.53 (dd, J=13.4, 6.9 Hz, 1H), 3.15-3.10 (m, 1H), 3.03-2.90 (m, 4H), 2.42 (s, 3H), 1.40 (s, 9H).

¹³C NMR (100 MHz, CDCl₃) δ 169.6, 155.0, 146.6, 144.3, 135.7, 133.7, 129.6, 129.4, 128.6, 128.1, 127.2, 101.8, 80.1, 54.4, 37.6, 37.0, 28.3, 21.6 ppm.

HRMS m/z (ESI) calcd for $C_{24}H_{31}N_2O_6S$ (M+H)⁺: 475.1903, found: 475.1901.

Embodiment 13

N-methyl-N-ethynyl methanesulfonamide (0.20 mmol) and Boc-L-leucine (0.2 mmol) are added to a clean 25 mL reaction tube, and an appropriate amount of dichloromethane is added as a solvent. The reaction is carried out at 20° C. for 40 minutes. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

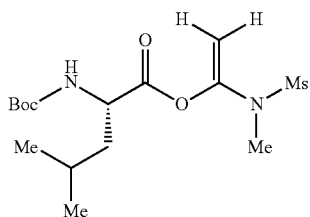 [SMILES: C=C(OC(=O)[C@H](CC(C)C)NC(=O)OC(C)(C)C)N(C)S(C)(=O)=O]

$^1$H NMR (400 MHz, CDCl$_3$) δ 5.05 (d, J=1.6 Hz, 1H), 4.90 (d, J=6.8 Hz, 1H), 4.84 (d, J=1.9 Hz, 1H), 4.29 (dd, J=13.4, 8.7 Hz, 1H), 3.08 (s, 3H), 2.98 (s, 3H), 1.78-1.50 (m, 3H), 1.41 (s, 9H), 0.97-0.92 (m, 6H);
$^{13}$C NMR (100 MHz, CDCl$_3$) δ 171.3, 155.4, 145.6, 100.7, 80.2, 52.2, 40.5, 37.5, 35.6, 28.2, 24.8, 22.8, 21.6 ppm;
HRMS m/z (ESI) calcd for C$_{15}$H$_{29}$N$_2$O$_6$S (M+H)$^+$: 365.1746, found 365.1743.

Embodiment 14

N-methyl-N-phenylethynyl p-toluenesulfonamide (0.20 mmol) and parachlorobenzoic-acid (0.2 mmol) are added to a clean 25 mL reaction tube, and an appropriate amount of dichloromethane is added as a solvent. The reaction is carried out at room temperature for 15 hours. TLC analysis is then performed. After the completion of the reaction, the solvent was concentrated off and the column chromatography are carried out to obtain a pure product, white solid, with a yield of 93%. The following are the structural formula of the product and the NMR data and mass spectrometry data of the product:

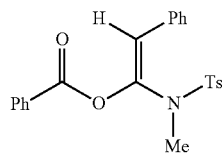 [SMILES: Cc1ccc(S(=O)(=O)N(C)/C(=C\c2ccccc2)OC(=O)c2ccccc2)cc1]

$^1$H NMR (400 MHz, CDCl$_3$) δ 7.82 (d, J=8.3 Hz, 2H), 7.70 (d, J=7.8 Hz, 2H), 7.65-7.55 (m, 3H), 7.43-7.37 (m, 4H), 7.34-7.28 (m, 1H), 7.02 (d, J=8.0 Hz, 2H), 6.35 (s, 1H), 3.14 (d, J=0.8 Hz, 3H), 2.24 (s, 3H);
$^{13}$C NMR (100 MHz, CDCl$_3$) δ 164.6, 143.6, 139.9, 136.0, 133.7, 131.9, 130.0, 129.4, 128.6, 128.6, 128.4, 128.3, 127.5, 119.3, 36.6, 21.3 ppm;
HRMS m/z (ESI) calcd for C$_{23}$H$_{22}$NO$_4$S (M+H)$^+$: 408.1270, found 408.1273.

Embodiment 15

N-methyl-N-phenylethynyl p-toluenesulfonamide (0.20 mmol) and parachlorobenzoic-acid (1.2 mmol) are added to a clean 25 mL reaction tube, and an appropriate amount of dichloromethane is added as a solvent. The reaction is carried out at 30° C. for 10 hours. TLC analysis is then performed. After the completion of the reaction, the solvent was concentrated off and the column chromatography are carried out to obtain a pure product, white solid, with a yield of 83%. The following are the structural formula of the product and the NMR data and mass spectrometry data of the product:

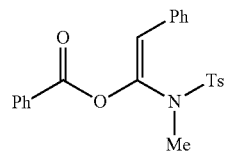

$^1$H NMR (400 MHz, CDCl$_3$) δ 7.82 (d, J=8.3 Hz, 2H), 7.70 (d, J=7.8 Hz, 2H), 7.65-7.55 (m, 3H), 7.43-7.37 (m, 4H), 7.34-7.28 (m, 1H), 7.02 (d, J=8.0 Hz, 2H), 6.35 (s, 1H), 3.14 (d, J=0.8 Hz, 3H), 2.24 (s, 3H);
$^{13}$C NMR (100 MHz, CDCl$_3$) δ 164.6, 143.6, 139.9, 136.0, 133.7, 131.9, 130.0, 129.4, 128.6, 128.5, 128.4, 128.3, 127.5, 119.3, 36.6, 21.3 ppm;
HRMS m/z (ESI) calcd for C$_{23}$H$_{22}$NO$_4$S (M+H)$^+$: 408.1270, found 408.1271.

Embodiment 16

N-methyl-N-ethynyl p-toluenesulfonamide (0.20 mmol) and parachlorobenzoic-acid (0.2 mmol) are added to a clean 25 mL reaction tube, and an appropriate amount of dichloromethane is added as a solvent. The reaction is carried out at room temperature for 1.5 hours. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

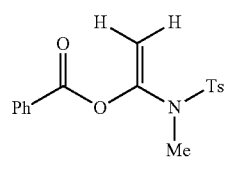

$^1$H NMR (400 MHz, CDCl$_3$) δ 7.86 (dd, J=8.2, 1.0 Hz, 2H), 7.74 (d, J=8.3 Hz, 2H), 7.61-7.55 (m, 1H), 7.41 (t, J=7.8 Hz, 2H), 7.28-7.23 (m, 2H), 5.03 (d, J=2.5 Hz, 1H), 4.88 (d, J=2.5 Hz, 1H), 3.10 (s, 3H), 2.38 (s, 3H);
$^{13}$C NMR (100 MHz, CDCl$_3$) δ 164.0, 146.8, 144.0, 134.3, 133.7, 130.1, 129.5, 128.6, 128.4, 127.9, 101.7, 37.1, 21.5 ppm;
HRMS m/z (ESI) calcd for C$_{17}$H$_{18}$NO$_4$S (M+H)$^+$: 332.0957, found 332.0956.

Embodiment 17

N-methyl-N-ethynyl p-toluenesulfonamide (0.20 mmol) and parachlorobenzoic-acid (0.2 mmol) are added to a clean 25 mL reaction tube, and an appropriate amount of dichloromethane is added as a solvent. The reaction is carried out at room temperature for 1.5 hours. TLC analysis is then performed. After the completion of the reaction, the solvent was concentrated off and the column chromatography are carried out to obtain a pure product, white solid, with a yield of 99%. The following are the structural formula of the product and the NMR data and mass spectrometry data of the product:

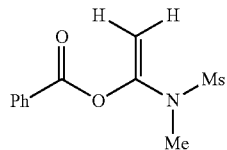

$^1$H NMR (400 MHz, CDCl$_3$) δ 8.09 (dd, J=8.3, 1.2 Hz, 2H), 7.68-7.60 (m, 1H), 7.50 (t, J=7.8 Hz, 2H), 5.15 (d, J=2.6 Hz, 1H), 4.99 (d, J=2.6 Hz, 1H), 3.18 (s, 3H), 3.03 (s, 3H);

$^{13}$C NMR (100 MHz, CDCl$_3$) δ 164.2, 146.1, 134.1, 130.1, 128.8, 128.3, 100.3, 37.7, 36.0 ppm;

HRMS m/z (ESI) calcd for C$_{11}$H$_{14}$NO$_4$S (M+H)$^+$: 256.0644, found 256.0645.

Embodiment 18

3-ethynyl-2-oxazolidinone (1.20 mmol) and benzoic acid (0.2 mmol) are added to a clean 25 mL reaction tube, and an appropriate amount of dichloromethane is added as a solvent. The reaction is carried out at 10° C. for 12 hours. TLC analysis is then performed. After the completion of the reaction, the solvent was concentrated off and the column chromatography are carried out to obtain a pure product, white solid, with a yield of 53%. The following are the structural formula of the product and the NMR data and mass spectrometry data of the product:

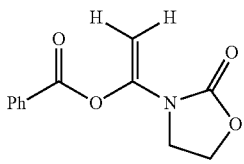

$^1$HNMR (400 MHz, CDCl$_3$) δ 8.16 (dd, J=8.4, 1.3 Hz, 2H), 7.76-7.70 (m, 1H), 7.60 (t, J=7.9 Hz, 2H), 5.05 (d, J=2.5 Hz, 1H), 4.81 (d, J=2.5 Hz, 1H), 4.40-4.36 (m, 2H), 3.83-3.79 (m, 2H);

$^{13}$C NMR (CDCl$_3$, 100 MHz) δ 165.2, 155.4, 137.6, 134.1, 132.1, 128.8, 128.6, 116.3, 63.1, 44.7 ppm;

HRMS (ESI) m/z calculated for C$_{12}$H$_{12}$NO$_4$ (M+H)$^+$: 234.0766 found: 234.0763.

Embodiment 19

N-methyl-N-ethynyl methanesulfonamide (0.03 mmol) and 6-carboxyfluorescein diacetate (0.03 mmol) are added to a clean 25 mL reaction tube, and an appropriate amount of dichloromethane is added as a solvent. The reaction is carried out at 30° C. for 4 hours. TLC analysis is then performed. After the completion of the reaction, the solvent was concentrated off and the column chromatography are carried out to obtain a pure product, white solid, with a yield of 90%. The following are the structural formula of the product and the NMR data and mass spectrometry data of the product:

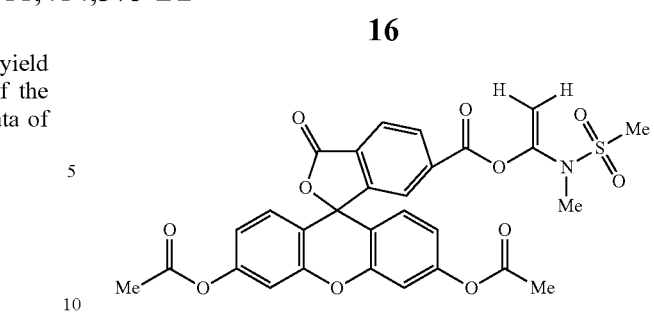

$^1$H NMR (400 MHz, CDCl$_3$) δ 8.38-8.31 (m, 1H), 8.14 (d, J=8.0 Hz, 1H), 7.85 (s, 1H), 7.13 (d, J=1.8 Hz, 2H), 6.85-6.81 (m, 4H), 5.09 (d, J=2.8 Hz, 1H), 4.96 (d, J=2.8 Hz, 1H), 3.14 (s, 3H), 2.97 (s, 3H), 2.32 (s, 6H).

$^{13}$C NMR (100 MHz, CDCl$_3$) δ 168.7, 167.8, 162.7, 153.3, 152.3, 151.5, 146.4, 135.1, 131.8, 130.3, 128.7, 125.9, 125.8, 118.0, 115.5, 110.6, 100.2, 81.9, 37.4, 36.4, 21.1 ppm.

LCMS m/z (ESI) calcd for C$_{29}$H$_{23}$NO$_{11}$S (M+H)$^+$: 594.11, found: 594.11.

Embodiment 20

N-methyl-N-ethynyl p-toluenesulfonamide (0.03 mmol) and 6-carboxyfluorescein diacetate (0.03 mmol) are added to a clean 25 mL reaction tube, and an appropriate amount of dichloromethane is added as a solvent. The reaction is carried out at 30° C. for 4 hours. TLC analysis is then performed. After the completion of the reaction, the solvent was concentrated off and the column chromatography are carried out to obtain a pure product, white solid, with a yield of 93%. The following are the structural formula of the product and the NMR data and mass spectrometry data of the product:

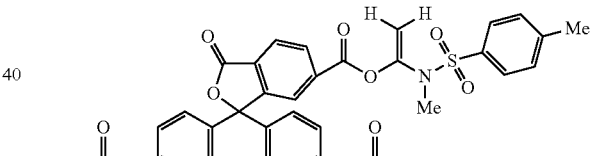

$^1$H NMR (400 MHz, CDCl$_3$) δ 8.14-8.09 (m, 1H), 8.01 (d, J=8.0 Hz, 1H), 7.74 (s, 1H), 7.61 (d, J=8.2 Hz, 2H), 7.16 (d, J=8.2 Hz, 2H), 7.06 (d, J=2.1 Hz, 2H), 6.80-6.71 (m, 4H), 4.86 (d, J=2.8 Hz, 1H), 4.60 (d, J=2.8 Hz, 1H), 2.97 (s, 3H), 2.31 (s, 3H), 2.23 (s, 6H).

$^{13}$C NMR (100 MHz, CDCl$_3$) δ 168.7, 167.8, 162.6, 152.9, 152.4, 151.6, 147.2, 144.3, 135.4, 133.6, 131.8, 130.3, 129.6, 128.8, 128.0, 125.9, 125.5, 118.0, 115.6, 110.6, 101.2, 82.1, 37.6, 21.5, 21.1 ppm.

LCMS m/z (ESI) calcd for C$_{35}$H$_{27}$NO$_{11}$S (M+H)$^+$: 670.14, found: 670.14.

Embodiment 21

N-methyl-N-ethynyl methanesulfonamide (0.03 mmol) and 4-dimethylamine azobenzene-4'-carboxylic acid (0.03 mmol) are added to a clean 25 mL reaction tube, and an appropriate amount of dichloromethane is added as a solvent. The reaction is carried out at 30° C. for 24 hours. TLC analysis is then performed. After the completion of the reaction, the solvent was concentrated off and the column chromatography are carried out to obtain a pure product, red solid, with a yield of 86%. The following are the structural formula of the product and the NMR data and mass spectrometry data of the product:

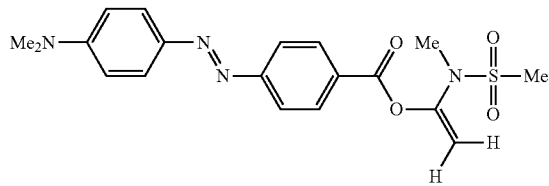 [SMILES: C=C(OC(=O)c1ccc(/N=N/c2ccc(N(C)C)cc2)cc1)N(C)S(C)(=O)=O]

¹H NMR (400 MHz, CDCl₃) δ 8.19-8.16 (m, 2H), 7.93-7.88 (m, 4H), 6.78-6.75 (m, 2H), 5.17 (d, J=2.6 Hz, 1H), 5.01 (d, J=2.5 Hz, 1H), 3.20 (s, 3H), 3.12 (s, 6H), 3.05 (s, 3H).

¹³C NMR (100 MHz, CDCl₃) δ 164.0, 156.8, 153.1, 146.2, 143.8, 131.2, 128.0, 125.8, 122.3, 111.5, 100.3, 40.3, 37.9, 36.0 ppm.

LCMS m/z (ESI) calcd for $C_{19}H_{22}N_4O_4S$ (M+H)⁺: 403.14, found: 403.14.

Embodiment 22

N-methyl-N-ethynyl p-toluenesulfonamide (0.03 mmol) and 4-dimethylamine azobenzene-4'-carboxylic acid (0.03 mmol) are added to a clean 25 mL reaction tube, and an appropriate amount of dichloromethane is added as a solvent. The reaction is carried out at 30° C. for 24 hours. TLC analysis is then performed. After the completion of the reaction, the solvent was concentrated off and the column chromatography are carried out to obtain a pure product, orange solid, with a yield of 89%. The following are the structural formula of the product and the NMR data and mass spectrometry data of the product:

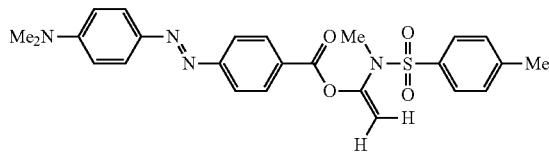 [SMILES: C=C(OC(=O)c1ccc(/N=N/c2ccc(N(C)C)cc2)cc1)N(C)S(=O)(=O)c1ccc(C)cc1]

¹HNMR (400 MHz, CDCl₃) δ 7.94-7.88 (m, 4H), 7.81 (d, J=8.6 Hz, 2H), 7.75 (d, J=8.2 Hz, 2H), 7.28-7.24 (m, 2H), 6.76 (d, J=9.1 Hz, 2H), 5.06 (d, J=2.4 Hz, 1H), 4.95 (d, J=2.4 Hz, 1H), 3.12 (s, 3H), 3.11 (s, 6H), 2.38 (s, 3H).

¹³C NMR (100 MHz, CDCl₃) δ 163.7, 156.6, 153.1, 146.8, 144.0, 143.8, 134.6, 131.1, 129.6, 128.4, 127.9, 125.7, 122.0, 111.5, 101.9, 40.3, 37.1, 21.5 ppm.

LCMS m/z (ESI) calcd for $C_{25}H_{26}N_4O_4S$ (M+H)⁺: 479.18, found: 479.18.

Embodiment 23

N-methyl-N-ethynyl p-toluenesulfonamide (0.15 mmol) and D-biotin (0.1 mmol) are added to a clean 25 mL reaction tube, and an appropriate amount of methanol is added as a solvent. The reaction is carried out at 30° C. for 48 hours. TLC analysis is then performed. After the completion of the reaction, the solvent was concentrated off and the column chromatography are carried out to obtain a pure product, colorless oily liquid, with a yield of 52%. The following are the structural formula of the product and the NMR data and mass spectrometry data of the product:

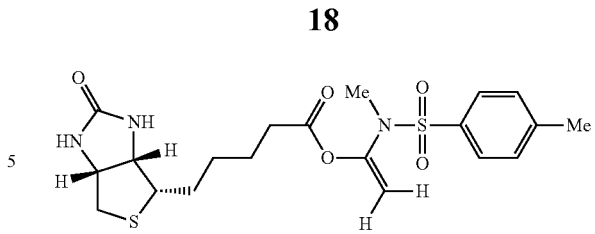

¹H NMR (400 MHz, DMSO-d₆) δ 7.69 (d, J=8.3 Hz, 2H), 7.46 (d, J=8.1 Hz, 2H), 6.49-6.35 (m, 2H), 4.78 (d, J=2.6 Hz, 1H), 4.69 (d, J=2.6 Hz, 1H), 4.35-4.29 (m, 1H), 4.17-4.11 (m, 1H), 3.13-3.06 (m, 1H), 2.95 (s, 3H), 2.86-2.80 (m, 1H), 2.63-2.57 (m, 1H), 2.42 (s, 3H), 2.33-2.27 (m, 2H), 1.66-1.23 (m, 6H).

¹³C NMR (100 MHz, DMSO-d₆) δ 171.0, 163.3, 146.8, 144.7, 134.1, 130.3, 128.0, 100.0, 61.5, 59.7, 55.8, 37.5, 33.5, 28.4, 28.3, 24.5, 21.5 ppm.

LCMS m/z (ESI) calcd for $C_{20}H_{27}N_3O_5S_2$ (M+Na)⁺: 476.13, found: 476.13.

The second part refers to specific embodiments (Embodiments 24 to 29) of use of an α-acyloxyenamide compound in the synthesis of an amide and a polypeptide, and the Applicant believes that Embodiment 29 is optimal.

Embodiment 24

Acetoxy-alkenylamide (0.20 mmol) and 2-phenylethyl-amine (0.3 mmol) are added to a clean 25 mL reaction tube, and an appropriate amount of dichloromethane is added as a solvent. The reaction is carried out at 30° C. for 1.5 hours. TLC analysis is then performed. After the completion of the reaction, the solvent was concentrated off and column chromatography are carried out to obtain a pure product, white solid, with a yield of 98%. The following are the structural formula of the product and the NMR data and mass spectrometry data of the product:

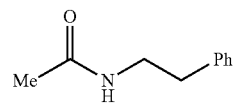

¹H NMR (400 MHz, CDCl₃) δ 7.27 (t, J=7.3 Hz, 2H), 7.21-7.16 (m, 3H), 6.50 (s, 1H), 3.45 (dd, J=13.3, 7.0 Hz, 2H), 2.79 (t, J=7.2 Hz, 2H), 1.90 (s, 3H).

¹³C NMR (100 MHz, CDCl₃) δ 170.2, 138.7, 128.4, 128.3, 126.1, 40.5, 35.3, 22.8 ppm.

HRMS m/z (ESI) calcd for $C_{10}H_{14}NO$ (M+H)⁺: 164.1075, found 164.1070.

Embodiment 25

1-(N-methyl-p-toluenesulfonylamino) vinyl acetate (0.20 mmol) and 2-phenylethylamine (2 mmol) are added to a clean 25 mL reaction tube, and an appropriate amount of dichloromethane is added as a solvent. The reaction is carried out at 40° C. TLC analysis is then performed. After the completion of the reaction, the solvent was concentrated off and column chromatography are carried out to obtain a pure product, white solid, with a yield of 90%. The following are the structural formula of the product and the NMR data and mass spectrometry data of the product:

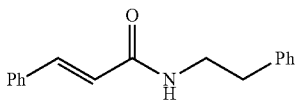 [SMILES: O=C(/C=C/c1ccccc1)NCCc1ccccc1]

¹H NMR (400 MHz, CDCl₃) δ 7.62 (d, J=15.6 Hz, 1H), 7.47 (dd, J=6.5, 2.9 Hz, 2H), 7.37-7.29 (m, 5H), 7.28-7.20 (m, 3H), 6.35 (d, J=15.6 Hz, 1H), 5.85 (s, 1H), 3.66 (dd, J=13.0, 6.8 Hz, 2H), 2.89 (t, J=6.9 Hz, 2H).
¹³C NMR (100 MHz, CDCl₃) δ 165.9, 141.0, 138.9, 134.8, 129.6, 128.8, 128.7, 128.6, 127.7, 126.5, 120.7, 40.8, 35.6 ppm.
FIRMS m/z (ESI) calcd for $C_{17}H_{18}NO$ (M+H)⁺: 252.1388, found 252.1385.

Embodiment 26

1-(N-methyl-p-toluenesulfonylamino)-vinyl phenyl acrylate (0.30 mmol) and 2-phenylethylamine (0.2 mmol) are added to a clean 25 mL reaction tube, and an appropriate amount of dichloromethane is added as a solvent. The reaction is carried out at 0° C. for 4 hours. TLC analysis is then performed. After the completion of the reaction, the solvent was concentrated off and column chromatography are carried out to obtain a pure product, white solid, with a yield of 99%. The following are the structural formula of the product and the NMR data and mass spectrometry data of the product:

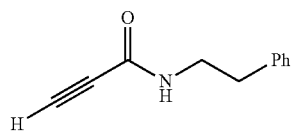 [SMILES: C#CC(=O)NCCc1ccccc1]

¹H NMR (400 MHz, CDCl₃) δ 7.33 (t, J=7.3 Hz, 2H), 7.27-7.18 (m, 3H), 5.94 (s, 1H), 3.57 (q, J=6.9 Hz, 2H), 2.85 (t, J=7.0 Hz, 2H), 2.75 (s, 1H).
¹³C NMR (100 MHz, CDCl₃) δ 152.1, 138.2, 128.7, 128.7, 126.7, 79.2, 73.1, 40.9, 35.2 ppm.
HRMS m/z (ESI) calcd for $C_{11}H_{12}NO$ (M+H)⁺: 174.0919, found 174.0916.

Embodiment 27

1-(N-methyl-p-toluenesulfonylamino) vinyl-benzothiophenecarboxylate (1.0 mmol) and 2-phenylethylamine (0.2 mmol) are added to a clean 25 mL reaction tube, and an appropriate amount of dichloromethane is added as a solvent. The reaction is carried out at 50° C. for 4 hours. TLC analysis is then performed. After the completion of the reaction, the solvent was concentrated off and column chromatography are carried out to obtain a pure product, white solid, with a yield of 98%. The following are the structural formula of the product and the NMR data and mass spectrometry data of the product:

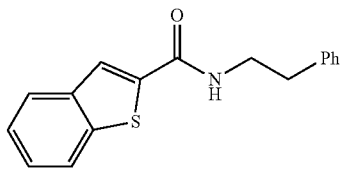 [SMILES: O=C(NCCc1ccccc1)c1cc2ccccc2s1]

¹H NMR (400 MHz, CDCl₃) δ 7.90-7.75 (m, 2H), 7.68 (s, 1H), 7.42-7.36 (m, 2H), 7.34-7.30 (m, 2H), 7.26-7.24 (m, 3H), 6.26 (s, 1H), 3.71 (dd, J=13.0, 6.8 Hz, 2H), 2.94 (t, J=6.9 Hz, 2H).
¹³C NMR (100 MHz, CDCl₃) δ 162.2, 140.7, 139.0, 138.7, 138.4, 128.8, 128.7, 126.6, 126.3, 125.1, 125.0, 124.9, 122.7, 41.3, 35.7 ppm.
HRMS m/z (ESI) calcd for $C_{17}H_{16}NOS$ (M+H)⁺: 282.0953, found 282.0950.

Embodiment 28

1-(N-methyl-p-toluenesulfonylamino) vinyl p-chlorobenzoate (0.20 mmol) and 2-morpholinylamine (0.2 mmol) are added to a clean 25 mL reaction tube, and an appropriate amount of dichloromethane is added as a solvent. The reaction is carried out at room temperature for 5 hours. TLC analysis is then performed. After the completion of the reaction, the solvent was concentrated off and column chromatography are carried out to obtain a pure product, white solid, with a yield of 98%. The following are the structural formula of the product and the NMR data and mass spectrometry data of the product:

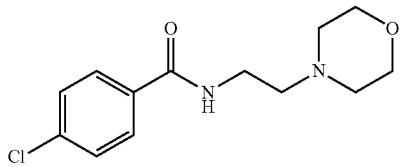 [SMILES: O=C(NCCN1CCOCC1)c1ccc(Cl)cc1]

¹H NMR (400 MHz, CDCl₃) δ 7.76-7.65 (m, 2H), 7.44-7.35 (m, 2H), 3.76-3.66 (m, 4H), 3.52 (dd, J=11.2, 5.8 Hz, 2H), 2.58 (t, J=6.0 Hz, 2H), 2.54-2.43 (m, 4H).
¹³C NMR (100 MHz, CDCl₃) δ 166.3, 137.6, 132.9, 128.8, 128.3, 66.9, 56.8, 53.3, 36.1 ppm.
HRMS m/z (ESI) calcd for $C_{13}H_{18}ClN_2O_2$ (M+H)⁺: 269.1057, found 269.1058.

Embodiment 29

1-(N-methyl-m ethanesulfonamido) vinyl-N-benzyloxycarbonyl-tryptophanate (0.2 mmol) and threonine tert-butyl ester (0.4 mmol) are added to a clean 25 mL reaction tube, and an appropriate amount of dichloromethane is added as a solvent. The reaction is carried out at room temperature for 15 hours. TLC analysis is then performed. After the completion of the reaction, the solvent was concentrated off and column chromatography are carried out to obtain a pure product, white solid, with a yield of 97%. The following are the structural formula of the product and the NMR data and mass spectrometry data of the product:

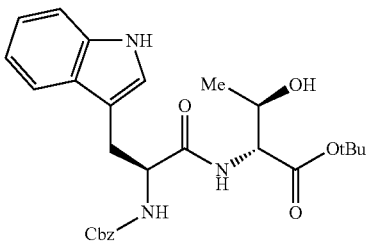 [SMILES: C[C@@H](O)[C@@H](NC(=O)[C@H](Cc1c[nH]c2ccccc12)NC(=O)OCc1ccccc1)C(=O)OC(C)(C)C]

$^1$H NMR (400 MHz, CDCl$_3$) δ 8.29 (s, 1H), 7.59 (d, J=7.5 Hz, 1H), 7.28-7.26 (m, 6H), 7.14 (t, J=7.5 Hz, 1H), 7.05 (t, J=7.4 Hz, 1H), 6.99 (s, 1H), 6.88 (d, J=6.2 Hz, 1H), 5.66 (s, 1H), 5.15-4.89 (m, 2H), 4.59 (d, J=4.9 Hz, 1H), 4.40 (dd, J=8.6, 3.2 Hz, 1H), 4.15-4.12 (m, 1H), 3.24 (d, J=5.3 Hz, 2H), 2.86 (s, 1H), 1.42 (s, 9H), 1.04 (d, J=5.3 Hz, 3H);

$^{13}$C NMR (100 MHz, CDCl$_3$) δ 172.0, 169.6, 156.2, 136.2, 128.4, 128.3, 128.0, 128.0, 127.5, 123.4, 122.1, 119.6, 118.6, 111.2, 110.1, 82.5, 68.3, 67.0, 58.2, 55.7, 28.1, 27.9, 19.8 ppm;

HRMS m/z (ESI) calcd for C$_{27}$H$_{34}$N$_3$O$_6$(M+H)$^+$: 496.2448, found 496.24484; de: >99%.

We have conducted extensive optimization regarding the racemization during the formation of dipeptides. Serine, which is highly prone to racemization upon activation, was selected as a model substrate to study the racemization by comparing the results with the currently widely used coupling reagents. From the results of Table 1, none of our ynamide coupling reagents such as MYMsA and MYTsA is observed to induce racemization in either an organic solvent or water. In contrast, coupling reagents such as DCC, HATU, HBTU and PyBop, commonly used at current, have very serious racemization. This result shows the advantages of the new coupling reagent ynamide developed by us in the synthesis of peptides.

The third part refers to Embodiments 30 to 39 of a method (one-pot method) for synthesizing an amide and a polypeptide by directly using a carboxylic acid and an amine compound as raw materials and under the mediation of ynamides, and the Applicant believes that Embodiment 36 is optimal.

Embodiment 30

0.2 mmol of 1-adamantanecarboxylic acid and an appropriate amount of dichloromethane are added to a clean 25 mL reaction tube, and then 0.22 mmol of N-methyl-N-ethynyl p-toluenesulfonamide is added; the mixture is stirred at room temperature for 0.5 hours, and TLC analysis is then performed; after the reaction is completed, 0.22 mmol of t-butylamine is added; the mixture is stirred at room temperature for 5 hours, and TLC analysis is then performed; after the reaction is completed, column chromatography is carried out for separation and purification to directly obtain a pure product, white solid, with a yield of 98%. The following are the structural formula of the product and the NMR data and mass spectrometry data of the product:

TABLE 1

Comparative study of ynamides and the conventional coupling reagents causing racemization in synthesis of dipeptides

| entry | coupling reagent | additive | solvent | time | yield | de |
| --- | --- | --- | --- | --- | --- | --- |
| 1 | HBTU | DIEA | DCM | 10 min | 90% | 64% |
| 2 | HATU | DIEA | DCM | 10 min | 70% | 74% |
| 3 | PyBop | DIEA | DCM | 10 min | 91% | 76% |
| 4 | DCC | — | DCM | 10 min | 98% | 82% |
| 5 | MYMsA | — | DCM | 22 h | 99% | >99% |
| 6 | MYTsA | — | DCM | 22 h | 94% | >99% |
| 7 | MYMsA | — | H$_2$O | 1.5 h | 96% | >99% |
| 8 | MYTsA | — | H$_2$O | 1.5 h | 95% | >99% |
| 9 | MYMsA | — | DMSO:H$_2$O 1:1 | 1.5 h | 96% | >99% |
| 10 | MYTsA | — | DMSO:H$_2$O 1:1 | 1.5 h | 96% | >99% |
| 11 | MYMsA | — | DMF:H$_2$O 1:1 | 2 h | 98% | >99% |
| 12 | MYTsA | — | DMF:H$_2$O 1:1 | 2 h | 97% | >99% |

Abbreviations in the table:
HBTU: benzotriazole-N, N, N', N'-tetramethylurea hexafluorophosphate;
HATU: 2-(7-azabenzotriazole)-N, N, N', N'-tetramethylurea hexafluorophosphate;
DCM: dichloromethane;
DIEA: N,N-diisopropylethylamine;
DCC: cyclohexylcarbodiimide;
MYMsA: N-methyl-N-ethynylmethanesulfonamide;
MYTsA: N-methyl-N-ethynyl p-toluenesulfonamide;
"—": no additive;
"de": diastereoselectivity.

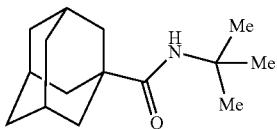 [SMILES: CC(C)(C)NC(=O)C12CC3CC(CC(C3)C1)C2]

¹H NMR (400 MHz, CDCl₃) δ 5.35 (br s, 1H), 2.01 (br s, 3H), 1.81-1.78 (m, 6H), 1.73-1.64 (m, 6H), 1.31 (s, 9H).

¹³C NMR (100 MHz, CDCl₃) δ 177.6, 50.7, 41.1, 39.6, 36.7, 29.0, 28.4 ppm.

HRMS m/z (ESI) calcd for $C_{15}H_{26}NO$ (M+H)⁺: 236.2014, found 236.2018.

Embodiment 31

0.2 mmol of phenylpropiolic acid and an appropriate amount of dichloromethane are added to a clean 25 mL reaction tube, and then 0.22 mmol of N-methyl-N-ethynyl p-toluenesulfonamide is added; the mixture is stirred at 0° C. for 30 minutes, and TLC analysis is then performed; after the reaction is completed, 0.5 mmol of tetrahydropyrrole is added; the mixture is stirred at room temperature for 0.5 hours, and TLC analysis is then performed; after the reaction is completed, column chromatography is carried out for separation and purification to directly obtain a pure product, white solid, with a yield of 99%. The following are the structural formula of the product and the NMR data and mass spectrometry data of the product:

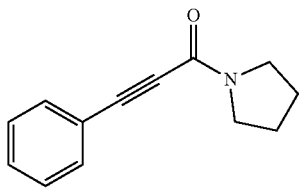 [SMILES: O=C(C#Cc1ccccc1)N1CCCC1]

¹H NMR (400 MHz, CDCl₃) δ 7.53 (d, J=6.8 Hz, 2H), 7.41-7.32 (m, 3H), 3.72 (t, J=6.4 Hz, 2H), 3.52 (t, J=6.6 Hz, 2H), 1.99-1.91 (m, 4H).

¹³C NMR (100 MHz, CDCl₃) δ 152.8, 132.5, 130.0, 128.6, 120.8, 88.8, 82.8, 48.2, 45.5, 25.5, 24.8 ppm.

HRMS m/z (ESI) calcd for $C_{13}H_{14}NO$ (M+H)⁺: 200.1075, found 200.1078.

Embodiment 32

0.2 mmol of phenylpropiolic acid and an appropriate amount of dichloromethane are added to a clean 25 mL reaction tube, and then 0.22 mmol of N-methyl-N-ethynyl p-toluenesulfonamide is added; the mixture is stirred at room temperature for 30 minutes, and TLC analysis is then performed; after the reaction is completed, 0.22 mmol of O-benzylhydroxylamine is added; the mixture is stirred at 40° C. for 14 hours, and TLC analysis is then performed; after the reaction is completed, column chromatography is carried out for separation and purification to directly obtain a pure product, white solid, with a yield of 90%. The following are the structural formula of the product and the NMR data and mass spectrometry data of the product:

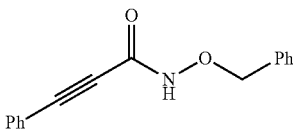 [SMILES: O=C(C#Cc1ccccc1)NOCc1ccccc1]

¹HNMR (400 MHz, CDCl₃) δ 9.14 (s, 1H), 7.49 (d, J=6.1 Hz, 2H), 7.45-7.24 (m, 8H), 4.97 (s, 2H).

¹³C NMR (100 MHz, CDCl₃) δ 151.9, 134.8, 132.5, 130.3, 129.2, 128.7, 128.5, 128.4, 119.6, 78.0, 78.4, 29.6 ppm.

HRMS m/z (ESI) calcd for $C_{16}H_{14}NO_2$ (M+H)⁺: 252.1025, found 252.1028.

Embodiment 33

0.2 mmol of phenylpropiolic acid and an appropriate amount of dichloromethane are added to a clean 25 mL reaction tube, and then 0.22 mmol of N-methyl-N-ethynyl methanesulfonamide is added; the mixture is stirred at 0° C. for 50 minutes, and TLC analysis is then performed; after the reaction is completed, 0.22 mmol of tryptamine is added; the mixture is stirred at room temperature for 40 hours, and TLC analysis is then performed; after the reaction is completed, column chromatography is carried out for separation and purification to directly obtain a pure product, white solid, with a yield of 99%. The following are the structural formula of the product and the NMR data and mass spectrometry data of the product:

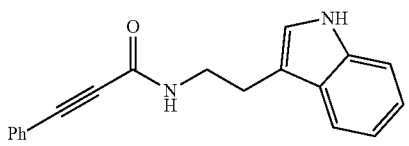 [SMILES: O=C(C#Cc1ccccc1)NCCc1c[nH]c2ccccc12]

¹H NMR (400 MHz, CDCl₃) δ 8.51 (s, 1H), 7.59 (d, J=7.8 Hz, 1H), 7.47-7.40 (m, 2H), 7.40-7.32 (m, 2H), 7.30-7.26 (m, 2H), 7.22-7.16 (m, 1H), 7.14-7.08 (m, 1H), 7.01 (d, J=2.1 Hz, 1H), 6.23 (s, 1H), 3.66 (dd, J=12.8, 6.7 Hz, 2H), 3.00 (t, J=6.7 Hz, 2H).

¹³C NMR (100 MHz, CDCl₃) δ 153.5, 136.4, 132.4, 129.9, 128.4, 127.1, 122.3, 122.0, 120.0, 119.3, 118.5, 112.1, 111.4, 84.7, 83.0, 40.1, 25.0 ppm.

HRMS m/z (ESI) calcd for $C_{19}H_{17}N_2O$ (M+H)⁺: 289.1341, found 289.1346.

Embodiment 34

0.2 mmol of phenylpropiolic acid and an appropriate amount of dichloromethane are added to a clean 25 mL reaction tube, and then 0.22 mmol of N-methyl-N-ethynyl methanesulfonamide is added; the mixture is stirred at room temperature for 10 minutes, and TLC analysis is then performed; after the reaction is completed, 0.22 mmol of diisopropylamine is added; the mixture is stirred at 40° C. for 14 minutes, and TLC analysis is then performed; after the reaction is completed, column chromatography is carried out for separation and purification to directly obtain a pure product, white solid, with a yield of 76%. The following are the structural formula of the product and the NMR data and mass spectrometry data of the product:

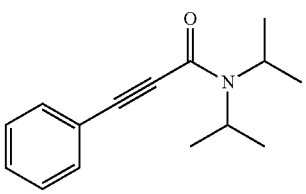 [SMILES: CC(C)N(C(=O)C#Cc1ccccc1)C(C)C]

$^1$H NMR (400 MHz, CDCl$_3$) δ 7.57-7.45 (m, 2H), 7.41-7.29 (m, 3H), 4.59 (s, 1H), 3.70 (s, 1H), 1.40 (d, J=6.8 Hz, 6H), 1.29 (d, J=6.8 Hz, 6H).

$^{13}$C NMR (100 MHz, CDCl$_3$) δ 153.5, 132.1, 129.6, 128.4, 121.0, 88.4, 83.1, 50.3, 45.7, 21.0, 20.1 ppm.

HRMS m/z (ESI) calcd for C$_{15}$H$_{20}$NO (M+H)$^+$: 230.1545, found 230.1559.

Embodiment 35

0.2 mmol of phenylpropiolic acid and an appropriate amount of dichloromethane are added to a clean 25 mL reaction tube, and then 0.22 mmol of N-methyl-N-ethynyl p-toluenesulfonamide is added; the mixture is stirred at room temperature for 10 minutes, and TLC analysis is then performed; after the reaction is completed, 0.22 mmol of cholamine is added; the mixture is stirred at room temperature for 0.5 hours, and TLC analysis is then performed; after the reaction is completed, column chromatography is carried out for separation and purification to directly obtain a pure product, white solid, with a yield of 95%. The following are the structural formula of the product and the NMR data and mass spectrometry data of the product:

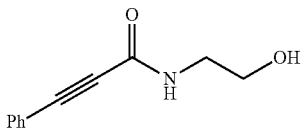 [SMILES: O=C(C#Cc1ccccc1)NCCO]

$^1$H NMR (400 MHz, CDCl$_3$) δ 7.52-7.46 (m, 2H), 7.37 (t, J=4.9 Hz, 1H), 7.30 (t, J=7.7 Hz, 2H), 6.92 (s, 1H), 3.75 (s, 2H), 3.49 (dd, J=10.5, 5.5 Hz, 2H).

$^{13}$C NMR (100 MHz, CDCl$_3$) δ 154.5, 132.6, 130.2, 128.6, 120.2, 85.6, 82.9, 61.4, 42.7 ppm HRMS m/z (ESI) calcd for C$_{11}$H$_{12}$NO$_2$ (M+H)$^+$: 190.0868, found 190.0867.

Embodiment 36

0.2 mmol of Fmoc-Asp(tBu)-OH and an appropriate amount of dichloromethane are added to a clean 25 mL reaction tube, and then 0.22 mmol of N-methyl-N-ethynyl methanesulfonamide is added; the mixture is stirred at room temperature for 30 minutes, and TLC analysis is then performed; after the reaction is completed, 0.22 mmol of H-Tyr(tBu)-OtBu is added; the mixture is stirred at 35° C. for 24 hours, and TLC analysis is then performed; after the reaction is completed, column chromatography is carried out for separation and purification to directly obtain a pure product, white solid, with a yield of 96%.

Alternatively, 0.2 mmol of Fmoc-Asp(tBu)-OH and an appropriate amount of dichloromethane are added to a clean 25 mL reaction tube, and then 0.22 mmol of N-methyl-N-ethynyl methanesulfonamide is added; the mixture is stirred at room temperature for 30 minutes, and TLC analysis is then performed. After the reaction is completed, the dichloromethane solvent is dried in a vacuum, an appropriate amount of water is then added as a solvent, and 0.22 mmol of H-Tyr(tBu)-OtBu is then added; the mixture is stirred at 35° C. for 1.5 hours, and TLC analysis is then performed; after the reaction is completed, column chromatography is carried out for separation and purification to directly obtain a pure product, white solid, with a yield of 98%.

The following are the structural formula of the product and the NMR data and mass spectrometry data of the product:

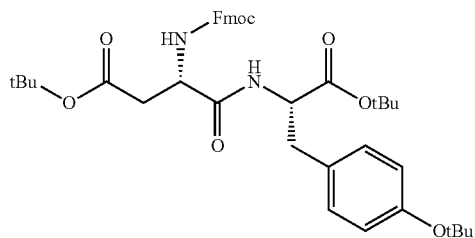

$^1$H NMR (400 MHz, CDCl$_3$) δ 7.76 (d, J=7.5 Hz, 2H), 7.59 (d, J=7.3 Hz, 2H), 7.39 (t, J=7.4 Hz, 2H), 7.31 (t, J=7.2 Hz, 2H), 7.07 (t, J=8.3 Hz, 3H), 6.89 (d, J=8.3 Hz, 2H), 5.99 (d, J=8.1 Hz, 1H), 4.66 (dd, J=13.4, 6.3 Hz, 1H), 4.55 (d, J=4.5 Hz, 1H), 4.38 (p, J=10.4 Hz, 2H), 4.23 (t, J=7.1 Hz, 1H), 3.10-2.96 (m, 2H), 2.90 (dd, J=17.0, 3.9 Hz, 1H), 2.63 (dd, J=16.7, 5.9 Hz, 1H), 1.45 (s, 9H), 1.36 (s, 9H), 1.29 (s, 9H).

$^{13}$C NMR (100 MHz, CDCl$_3$) δ 171.0, 169.9, 169.9, 155.9, 154.3, 143.6, 141.2, 130.9, 129.9, 127.7, 127.0, 125.0, 124.0, 119.9, 82.2, 81.8, 78.2, 67.3, 54.0, 51.0, 47.0, 37.4, 37.4, 28.7, 28.0, 27.8 ppm.

HRMS m/z (ESI) calcd for C$_{40}$H$_{51}$N$_2$O$_8$ (M+H)$^+$: 687.3645, found 687.3650.de: >99%.

Embodiment 37

0.2 mmol of Fmoc-Trp(tBu)-OH and an appropriate amount of dichloromethane are added to a clean 25 mL reaction tube, and then 0.22 mmol of N-methyl-N-ethynyl methanesulfonamide is added; the mixture is stirred at room temperature for 50 minutes, and TLC analysis is then performed; after the reaction is completed, 0.22 mmol of H-Tyr(tBu)-OtBu is added; the mixture is stirred at room temperature for 23 hours, and TLC analysis is then performed; after the reaction is completed, column chromatography is carried out for separation and purification to directly obtain a pure product, white solid, with a yield of 97%.

Alternatively, 0.2 mmol of Fmoc-Trp(tBu)-OH and an appropriate amount of dichloromethane are added to a clean 25 mL reaction tube, and then 0.22 mmol of N-methyl-N-ethynyl methanesulfonamide is added; the mixture is stirred at room temperature for 50 minutes, and TLC analysis is then performed. After the reaction is completed, the dichloromethane solvent is dried in a vacuum, an appropriate amount of a mixture of water and dimethylsulfoxide (which are in a ratio of 1:1) is then added as a solvent, and 0.22 mmol of H-Tyr(tBu)-OtBu is then added; the mixture is stirred at room temperature for 1 hour, and TLC analysis is then performed; after the reaction is completed, column chromatography is carried out for separation and purification to directly obtain a pure product, white solid, with a yield of 96%.

The following are the structural formula of the product and the NMR data and mass spectrometry data of the product:

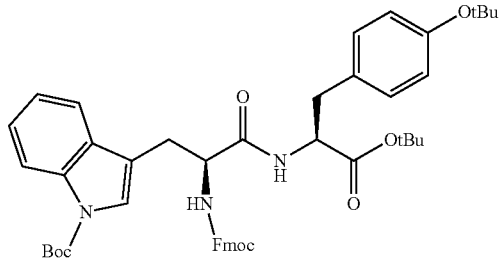

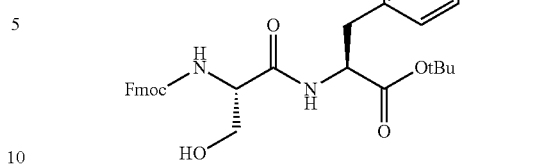

$^1$H NMR (400 MHz, CDCl$_3$) δ 8.14 (d, J=7.3 Hz, 1H), 7.75 (d, J=7.5 Hz, 2H), 7.62 (d, J=7.0 Hz, 1H), 7.57-7.49 (m, 3H), 7.42-7.27 (m, 5H), 7.25-7.21 (m, 1H), 6.85 (d, J=7.3 Hz, 2H), 6.77 (d, J=8.3 Hz, 2H), 6.36 (d, J=6.2 Hz, 1H), 5.50 (s, 1H), 4.55 (dd, J=12.8, 6.0 Hz, 2H), 4.46-4.37 (m, 1H), 4.37-4.29 (m, 1H), 4.20 (t, J=6.7 Hz, 1H), 3.34-3.21 (m, 1H), 3.14 (dd, J=14.2, 7.0 Hz, 1H), 2.94 (d, J=5.4 Hz, 2H), 1.60 (s, 9H), 1.30 (s, 9H), 1.26 (s, 9H).

$^{13}$C NMR (100 MHz, CDCl$_3$) δ 170.1, 169.7, 155.9, 154.3, 149.4, 143.7, 143.7, 141.2, 135.5, 130.7, 130.2, 129.8, 127.7, 127.1, 125.1, 124.7, 124.6, 123.9, 122.8, 119.9, 118.9, 115.4, 115.1, 83.6, 82.3, 78.3, 67.3, 55.0, 53.9, 47.0, 37.3, 28.8, 28.2, 28.1, 27.8 ppm.

HRMS m/z (ESI) calcd for C$_{48}$H$_{56}$N$_3$O$_8$ (M+H)$^+$: 802.4067, found 802.4065.de: >99%.

Embodiment 38

0.2 mmol of Fmoc-Ser-OH and an appropriate amount of dichloromethane are added to a clean 25 mL reaction tube, and then 0.22 mmol of N-methyl-N-ethynyl methanesulfonamide is added; the mixture is stirred at room temperature for 45 minutes, and TLC analysis is then performed; after the reaction is completed, 0.22 mmol of H-Tyr(tBu)-OtBu is added; the mixture is stirred at 35° C. for 19 hours, and TLC analysis is then performed; after the reaction is completed, column chromatography is carried out for separation and purification to directly obtain a pure product, white solid, with a yield of 98%.

Alternatively, 0.2 mmol of Fmoc-Ser-OH and an appropriate amount of dichloromethane are added to a clean 25 mL reaction tube, and then 0.22 mmol of N-methyl-N-ethynyl methanesulfonamide is added; the mixture is stirred at room temperature for 45 minutes, and TLC analysis is then performed. After the reaction is completed, the dichloromethane solvent is dried in a vacuum, an appropriate amount of a mixture of water and N,N-dimethylformamide (which are in a ratio of 1:1) is then added as a solvent, and 0.22 mmol of H-Tyr(tBu)-OtBu is then added; the mixture is stirred at 35° C. for 1 hour, and TLC analysis is then performed; after the reaction is completed, column chromatography is carried out for separation and purification to directly obtain a pure product, white solid, with a yield of 98%.

The following are the structural formula of the product and the NMR data and mass spectrometry data of the product:

$^1$H NMR (400 MHz, CDCl$_3$) δ 7.76 (d, J=7.5 Hz, 2H), 7.60 (d, J=7.3 Hz, 2H), 7.39 (t, J=7.4 Hz, 2H), 7.34-7.28 (m, 2H), 7.04 (d, J=8.4 Hz, 2H), 6.95 (s, 1H), 6.88 (d, J=8.4 Hz, 2H), 5.84 (s, 1H), 4.70 (dd, J=14.1, 6.4 Hz, 1H), 4.47-4.33 (m, 2H), 4.22 (t, J=7.0 Hz, 2H), 4.01 (d, J=10.1 Hz, 1H), 3.64 (d, J=5.0 Hz, 1H), 3.29 (s, 1H), 3.03 (qd, J=14.1, 6.4 Hz, 2H), 1.39 (s, 9H), 1.29 (s, 9H).

$^{13}$C NMR (100 MHz, CDCl$_3$) δ 170.6, 170.4, 156.4, 154.4, 143.7, 143.6, 141.3, 130.7, 129.8, 127.7, 127.1, 125.1, 124.1, 120.0, 82.7, 78.4, 67.3, 62.9, 55.3, 54.0, 47.0, 37.1, 28.8, 27.9 ppm.

HRMS m/z (ESI) calcd for C$_{35}$H$_{43}$N$_2$O$_7$ (M+H)$^+$: 603.3070, found 603.3070.de:>99%.

Embodiment 39

0.2 mmol of Z-Ser-OH and an appropriate amount of dichloromethane are added to a clean 25 mL reaction tube, and then 0.22 mmol of N-methyl-N-ethynyl methanesulfonamide is added; the mixture is stirred at room temperature for 40 minutes, and TLC analysis is then performed; after the reaction is completed, 0.22 mmol of H-Tyr(tBu)-OtBu is added; the mixture is stirred at 35° C. for 10 hours, and TLC analysis is then performed; after the reaction is completed, column chromatography is carried out for separation and purification to directly obtain a pure product, white solid, with a yield of 98%.

Alternatively, 0.2 mmol of Z-Ser-OH and an appropriate amount of dichloromethane are added to a clean 25 mL reaction tube, and then 0.22 mmol of N-methyl-N-ethynyl methanesulfonamide is added; the mixture is stirred at room temperature for 40 minutes, and TLC analysis is then performed. After the reaction is completed, the dichloromethane solvent is dried in a vacuum, an appropriate amount of water is then added as a solvent, and 0.22 mmol of H-Tyr(tBu)-OtBu is then added; the mixture is stirred at 35° C. for 0.5 hours, and TLC analysis is then performed; after the reaction is completed, column chromatography is carried out for separation and purification to directly obtain a pure product, white solid, with a yield of 96%.

The following are the structural formula of the product and the NMR data and mass spectrometry data of the product:

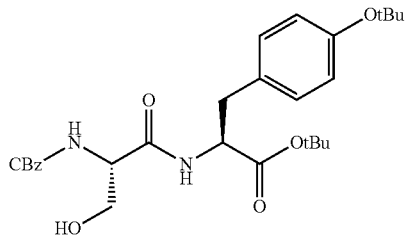

$^1$H NMR (400 MHz, CDCl$_3$) δ 7.43-7.29 (m, 5H), 7.04 (d, J=8.4 Hz, 2H), 6.96 (d, J=7.3 Hz, 1H), 6.92-6.85 (m, 2H), 5.79 (d, J=7.3 Hz, 1H), 5.16-5.03 (m, 2H), 4.69 (dd, J=14.2, 6.4 Hz, 1H), 4.23 (s, 1H), 4.08-3.92 (m, 1H), 3.61 (dt, J=11.5, 6.9 Hz, 1H), 3.24 (s, 1H), 3.02 (qd, J=14.0, 6.4 Hz, 2H), 1.39 (s, 9H), 1.31 (s, 9H).

$^{13}$C NMR (100 MHz, CDCl$_3$) δ 170.6, 170.5, 156.4, 154.4, 136.1, 130.8, 129.9, 128.6, 128.3, 128.1, 124.2, 82.7, 78.5, 67.3, 62.9, 55.4, 54.0, 37.2, 28.8, 28.0 ppm.

HRMS m/z (ESI) calcd for C$_{28}$H$_{39}$N$_2$O$_7$ (M+H)$^+$: 515.2757, found 515.2759.de:>99%.

The embodiments described above are only intended to describe the preferred embodiments of the invention, and are not intended to limit the scope of the invention, and various variants and modifications made to the technical solutions of the invention by those skilled in the art without departing from the design concept of the invention shall fall within the scope of the claims of the invention.

What is claimed is:

1. A method for synthesizing an amide and a polypeptide by directly using a carboxylic acid and an amine compound as raw materials and under the mediation of a ynamide, comprising the following steps:
   (1) adding 0.2-2 mmol of a carboxylic acid and an appropriate amount of dichloromethane solvent to a clean reaction tube, and then adding 0.2-2 mmol of a ynamide, and stirring at a temperature of 0-50° C.;
   (2) detecting the previous step of the reaction by using a TLC analysis; after the previous step of the reaction is completed, directly adding 0.2-2 mmol of an amine compound, or removing the dichloromethane solvent used in the previous step and adding water as a solvent and then adding 0.2-2 mmol of an amine compound, and then stirring at a temperature of 0-50° C.; and
   (3) detecting the previous step of the reaction by using a TLC analysis; after the previous step of the reaction is completed, and separating and purifying by column chromatography to directly obtain an amide compound; wherein the chemical reaction formula of Step (1) and Step (2) is:

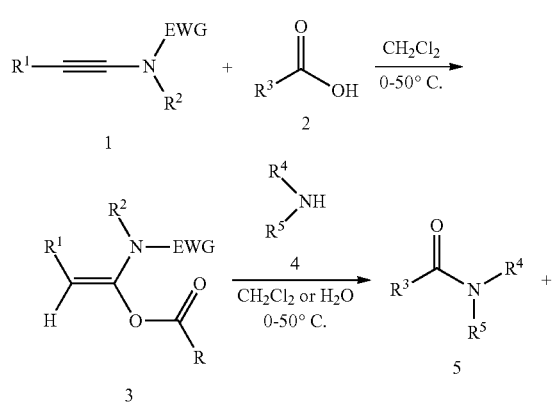

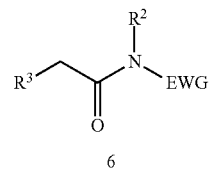

in the formula, 1 represents a ynamide, 2 represents a carboxylic acid, 3 represents an α-acyloxyenamide compound, 4 represents an amine compound, 5 represents an amide compound, 6 represents an amide by-product; le is selected from hydrogen, an alkyl group, an aryl group, an alkoxy group, an aryloxy group, an alkylthio group, an arylthio group, and the like; the EWG (electron-withdrawing group) is selected from an alkylsulfonyl group, an arylsulfonyl group, an aryl group, an carbonyl group, a nitro group, a nitrile group, a phosphono group, a sulfonimide, and the like; R$^2$ may be alkyl or aryl; R$^3$ is selected from an alkyl group, an aryl group, an alkenyl group, an alkynyl group, and the like; R$^4$ is selected from a hydrogen atom, an aliphatic substituent and an aromatic substituent; R$^5$ is selected from hydrogen, an aliphatic substituent, and an aromatic substituent.

2. The method for synthesizing an amide and a polypeptide by directly using a carboxylic acid and an amine compound as raw materials and under the mediation of a ynamide according to claim 1, wherein the carboxylic acid is selected from the group consisting of an aliphatic acid, an aromatic acid, a heterocyclic acid, an acetylenic acid, an olefine acid, an α-amino acid, and a β-amino acid.

3. The method for synthesizing an amide and a polypeptide by directly using a carboxylic acid and an amine compound as raw materials and under the mediation of a ynamide according to claim 1, wherein the ratio of the carboxylic acid to the ynamide to the amine compound is 1:1.2:1.2.

4. The method for synthesizing an amide and a polypeptide by directly using a carboxylic acid and an amine compound as raw materials and under the mediation of a ynamide according to claim 1, wherein the dichloromethane solvent is replaced with an organic solvent.

5. The method for synthesizing an amide and a polypeptide by directly using a carboxylic acid and an amine compound as raw materials and under the mediation of a ynamide according to claim 1, wherein water used as a solvent in Step (2) is replaced with a mixture of water and dimethylsulfoxide or a mixture of water and N,N-dimethylformamide.

6. The method for synthesizing an amide and a polypeptide by directly using a carboxylic acid and an amine compound as raw materials and under the mediation of a ynamide according to claim 1, wherein the temperature in Step (1) is 25° C. and the temperature in Step (2) is 35° C.

7. The method for synthesizing an amide and a polypeptide by directly using a carboxylic acid and an amine compound as raw materials and under the mediation of a ynamide according to claim 4, wherein the organic solvent is chloroform or 1,2-dichloroethane.

* * * * *